US006986741B2

(12) United States Patent
Poliac et al.

(10) Patent No.: US 6,986,741 B2
(45) Date of Patent: Jan. 17, 2006

(54) METHOD FOR MEASUREMENT OF SYSTOLIC AND DIASTOLIC TIME INTERVALS

(75) Inventors: Marius O. Poliac, St. Paul, MN (US); Liviu C. Poliac, Minneapolis, MN (US); Timothy J. O'Malley, Topsfield, MA (US)

(73) Assignee: Medwave, Inc., Danvers, MA (US)

( * ) Notice: Subject to any disclaimer, the term of this patent is extended or adjusted under 35 U.S.C. 154(b) by 0 days.

(21) Appl. No.: 10/409,669

(22) Filed: Apr. 8, 2003

(65) Prior Publication Data

US 2003/0216653 A1 Nov. 20, 2003

Related U.S. Application Data

(60) Provisional application No. 60/370,685, filed on Apr. 8, 2002.

(51) Int. Cl.
*A61B 5/02* (2006.01)
(52) U.S. Cl. .................................. 600/485; 600/500
(58) Field of Classification Search ........ 600/500–503, 600/481, 483, 485, 486, 490, 492–496
See application file for complete search history.

(56) References Cited

U.S. PATENT DOCUMENTS

| 4,203,451 A | * | 5/1980 | Panico ..................... 600/485 |
| 5,054,494 A | * | 10/1991 | Lazzaro et al. ............. 600/490 |
| 5,265,011 A | * | 11/1993 | O'Rourke .................. 600/485 |
| 5,365,933 A | * | 11/1994 | Elghazzawi ................. 600/510 |
| 5,445,159 A | * | 8/1995 | Cheng ....................... 600/485 |
| 5,450,852 A | | 9/1995 | Archibald et al. |
| 5,640,964 A | | 6/1997 | Archibald et al. |
| 5,642,733 A | | 7/1997 | Archibald et al. |
| 5,647,369 A | * | 7/1997 | Petrucelli et al. ........... 600/526 |
| 5,649,542 A | | 7/1997 | Archibald et al. |
| 5,720,292 A | | 2/1998 | Poliac |
| 5,722,414 A | | 3/1998 | Archibald et al. |
| 5,738,103 A | | 4/1998 | Poliac |
| 5,797,850 A | | 8/1998 | Archibald et al. |
| 5,941,828 A | | 8/1999 | Archibald et al. |
| 6,132,382 A | | 10/2000 | Archibald et al. |
| 6,171,242 B1 | * | 1/2001 | Amano et al. .............. 600/423 |
| 6,241,679 B1 | | 6/2001 | Curran |
| 6,245,022 B1 | | 6/2001 | Archibald et al. |
| 6,331,159 B1 | * | 12/2001 | Amano et al. .............. 600/300 |
| 6,340,349 B1 | | 1/2002 | Archibald et al. |
| D458,375 S | | 6/2002 | Thede |
| 6,471,646 B1 | | 10/2002 | Thede |
| 6,610,018 B1 | * | 8/2003 | McIntyre ................... 600/485 |
| 6,652,465 B2 | * | 11/2003 | Ogura ....................... 600/490 |
| 2002/0103442 A1 | * | 8/2002 | Mulligan et al. ........... 600/513 |

OTHER PUBLICATIONS

Belani K.G., Can J. Anesth, Accuracy of Radial Artery Blood Pressure Determination With the Vasotrac, 1999, pp 488-496.

Weissler A.M., JACC, Interpreting Systolic Timer Intervals in Man, 1983, pp. 1019-1020.

(Continued)

*Primary Examiner*—Robert L. Nasser
*Assistant Examiner*—Navin Natnithithadha
(74) *Attorney, Agent, or Firm*—Altera Law Group, LLC

(57) ABSTRACT

A method and apparatus for determining cardiac time intervals that can measure physiological data noninvasively. Arterial pulse values are measured either invasively or noninvasively, from which left ventricular waveform data is generated. Systolic and diastolic time intervals are derived based on the left ventricular waveform data.

17 Claims, 5 Drawing Sheets

OTHER PUBLICATIONS

Vivekananthan, K., The American Journal of Cardiology, Usefulness of the Combined Index of Systolic and Diastolic Myocardial Performance to Identify Cardiac Allograft Rejection, vol. 90, Sep. 1, 2002, pp. 517-520.

* cited by examiner

|  | IVCT | LVET | IVRT |
|---|---|---|---|
| BASELINE | 0.05(0.01) | 0.18(0.02) | 0.13(0.05) |
| ISOPROTERENOL | 0.03(0.01) | 0.17(0.02) | 0.07(0.03)* |
| NITROPRUSSIDE | 0.04(0.01) | 0.18(0.02) | 0.10((0.03)* |
| PHENYLEPHRINE | 0.06(0.02) | 0.21(0.08) | 0.18(0.05)* |

Fig. 5

METHOD FOR MEASUREMENT OF SYSTOLIC AND DIASTOLIC TIME INTERVALS

This application claims priority from U.S. Provisional Application No. 60/370,685 filed Apr. 8, 2002 for METHOD FOR MEASUREMENT OF SYSTOLIC AND DIASTOLIC TIME INTERVALS.

BACKGROUND OF THE INVENTION

The present invention relates to systems for measuring systolic and diastolic time intervals. In particular, the invention relates to a method and apparatus for noninvasively determining systolic and diastolic time intervals.

The heart goes through cyclic changes as it contracts and relaxes. Systole is the contraction of cardiac muscle and diastole is the relaxation of cardiac muscle. Both are ventricular by convention. The cardiac cycle is commonly divided into four phases. Filling occurs when the ventricles fill with blood via open atrio-ventricular (A-V) valves. Isovolumic contraction occurs when the ventricles contract and generate pressure, which closes the A-V valves, but the volume does not change. Ejection occurs when the ventricular pressures exceed aortic/pulmonary atrial pressures, and the respective aortic/pulmonic valves open and blood is ejected. Isovolumic relaxation occurs when ventricular pressures fall below aortic/pulmonary arterial pressures, the respective valves then close, and ventricular pressures continue to fall without changing volume. This continues until ventricular pressures fall below pulmonary venous/central venous pressures.

During diastole, the mitral valve is open so that the left atrial and left ventricular pressures are equal. In late diastole, left atrial contraction causes a small rise in pressure in both the left atrium and left ventricle. The onset of ventricular mechanical systole is marked by the initiation of left ventricular contraction. As the left ventricular pressure rises and exceeds that of the left atrium, the mitral valve closes, contributing to the first heart sound. As left ventricular pressure rises above the aortic pressure, the aortic valve opens, which is a silent event. As the ventricle begins to relax and its pressure falls below that of the aorta, the aortic valve closes, contributing to the second heart sound. As left ventricular pressure falls further below that of the left atrium, the mitral valve opens, which is another silent event in the normal heart. These cardiac time intervals can provide important insights into cardiac disease states.

One approach to early detection of cardiovascular disease is through measuring changes in systolic and diastolic time intervals. Present methods require highly invasive procedures that are expensive and risky to the patient. A less invasive or noninvasive procedure for measuring cardiac time intervals would be very advantageous to both the cost and risk factor.

Medwave, Inc. the assignee of the present invention, has developed non-invasive blood pressure measurement methods and devices which are described in the following United States patents and applications, hereby incorporated by reference: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; U.S. Pat. No. 5,797,850 entitled METHOD AND APPARATUS FOR CALCULATING BLOOD PRESSURE OF AN ARTERY; U.S. Pat. No. 5,941,828 entitled HAND-HELD NON-INVASIVE BLOOD PRESSURE MEASUREMENT DEVICE; U.S. Pat. No. 6,132,382 entitled NON-INVASIVE BLOOD PRESSURE SENSOR WITH MOTION ARTIFACT REDUCTION; U.S. Pat. No. 6,241,679 entitled NON-INVASIVE BLOOD PRESSURE SENSING DEVICE AND METHOD USING TRANSDUCER WITH ASSOCIATED MEMORY; U.S. Pat. No. 6,245,022 entitled NON-INVASIVE BLOOD PRESSURE SENSOR WITH MOTION ARTIFACE REDUCTION AND CONSTANT GAIN ADJUSTMENT DURING PRESSURE PULSES; U.S. Pat. No. 6,340,349 entitled HAND-FIELD NON-INVASIVE BLOOD PRESSURE MEASUREMENT DEVICE; U.S. Pat. No. 6,471,646 entitled BLOOD PRESSURE COLLECTION SYSTEM; U.S. Pat. No. D458,375 entitled BLOOD PRESSURE SENSOR; U.S. application Ser. No. 09/721,216 entitled WRIST-MOUNTED BLOOD PRESSURE MEASUREMENT DEVICE; U.S. application Ser. No. 09/594,051 entitled METHOD AND APPARATUS FOR CALCULATING BLOOD PRESSURE OF AN ARTERY; and U.S. application Ser. No. 10/081,574 entitled DISPOSABLE NON-INVASIVE BLOOD PRESSURE SENSOR. The Vasotrac system by MedWave Inc. measures, noninvasively and continuously, radial pulse blood pressure values and displays the radial pulse wave characteristics.

Information on cardiac time intervals and their applicability to noninvasively assess cardiac function has been the focus of numerous studies. For instance, Vivekananthan et. al. showed that noninvasive diagnostic markers may be clinically useful in evaluating and following cardiac allograft rejection. (Am J Cardiol 2002; 90:517–520). Increased efforts have been directed in extracting valuable diagnostic information from noninvasive means of physiological parameter monitoring.

BRIEF SUMMARY OF THE INVENTION

The present invention is a method of and apparatus for determining the cardiac time intervals of a person. Arterial pulse values are measured and used to generate left ventricular waveform data. Main cardiac events are identified from the left ventricular waveform data, from which systolic and diastolic time intervals are derived.

In the preferred embodiment, arterial pulse blood pressure values are measured noninvasively. However, arterial pulse blood pressure values may be measured invasively while still being advantageous to the patient.

BRIEF DESCRIPTION OF THE DRAWINGS

FIG. 5 is a table of experimental results showing changes in cardiac time intervals.

DETAILED DESCRIPTION

The present invention uses an arterial pressure waveform to estimate essential points on a left ventricular (LV) pressure waveform. Arterial pressure waveform data may be collected invasively using an arterial line or A-line. In the preferred embodiment of the present invention, however, arterial pressure waveform data is measured noninvasively. The Medwave Vasotrac system, described previously, is one method of accurately measuring arterial pressure waveform data noninvasively. With the present invention, cardiac time intervals can be monitored continuously and noninvasively.

Figure 1:
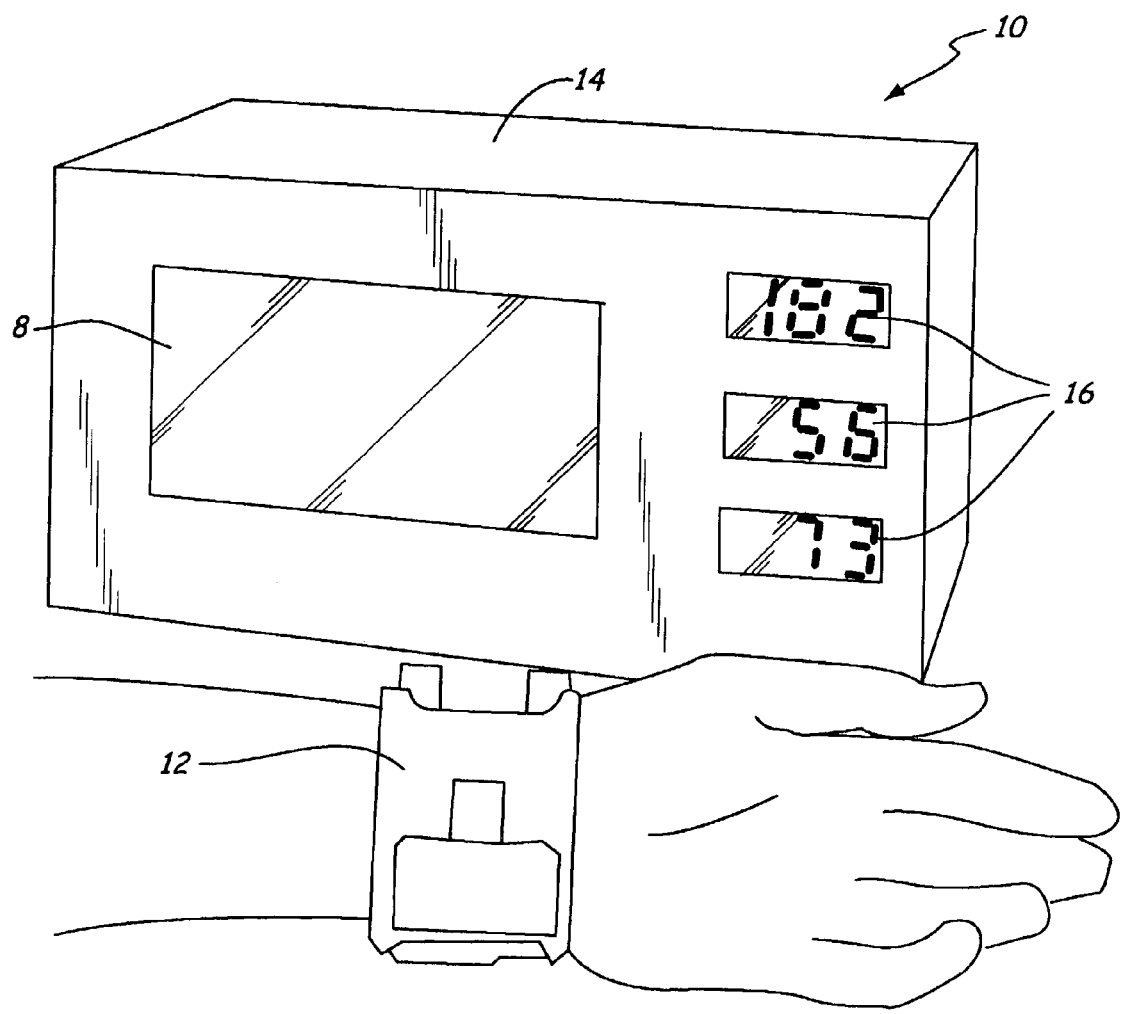
FIG. 1 shows a wrist-mounted blood pressure measurement device on a patient.

FIG. 1 shows a Vasotrac wrist-mounted blood pressure measurement device on a patient. Measurement device 10 includes sensor 12 and monitor 14. Monitor 14 further includes numerical displays 16 and waveform display 18.

In operation, sensor 12 is mounted onto a patient's wrist over the radial artery. Sensor 12 senses the radial blood pressure. Numerical displays 16 show systolic, diastolic, and mean pressure values, and waveform display 18 shows the arterial waveform and pulse rate. The information can be transferred from measurement device 10 to another device, such as a computer with appropriate software, for analysis.

Figure 2:
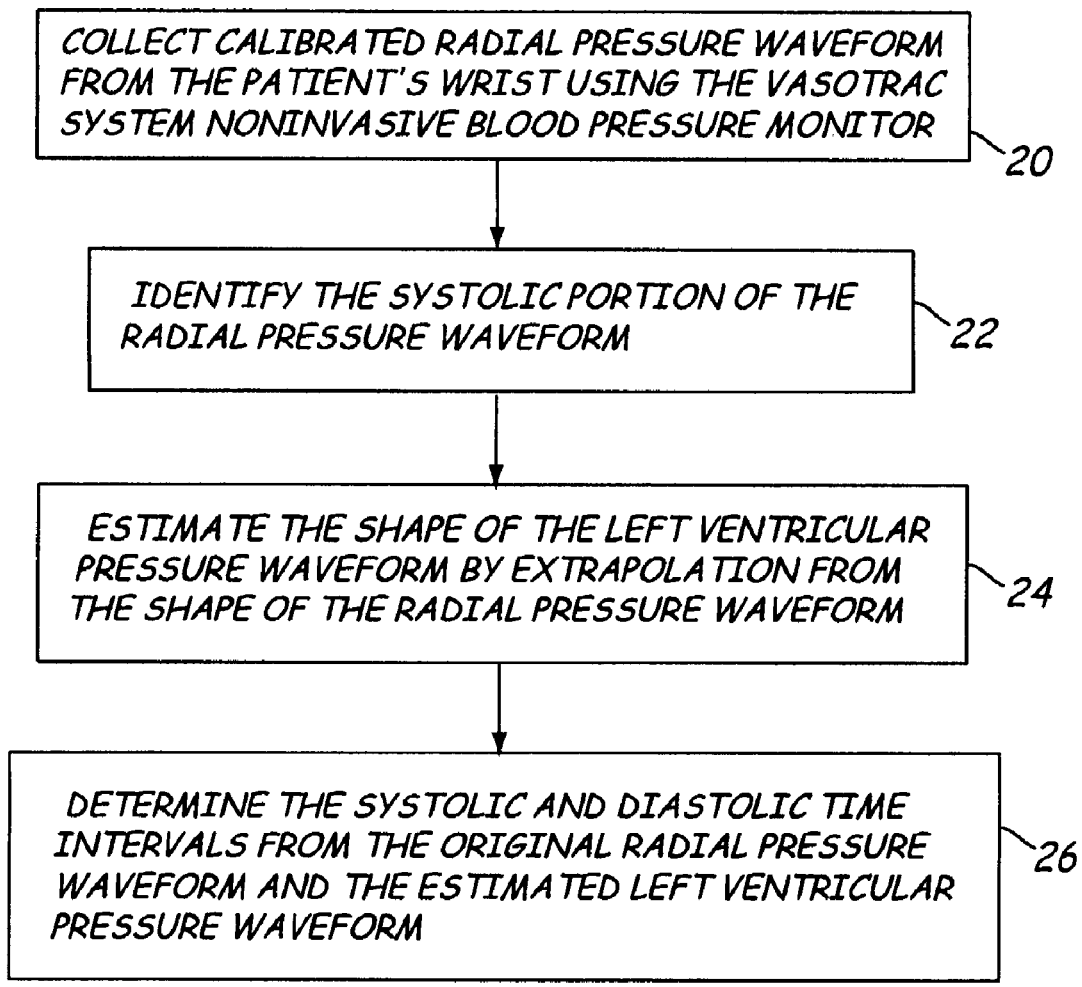
FIG. 2 is a flowchart illustrating operation of the preferred embodiment of the invention.

FIG. 2 is a flowchart of the preferred embodiment of the present invention. First, a calibrated Radial Pressure waveform is collected from the patient's wrist using measurement device 10 (Step 20). Next, the systolic portion of the Radial Pressure waveform is identified (Step 22). Then, the shape of the LV Pressure waveform is estimated by extrapolation from the shape of the Radial Pressure waveform (Step 24). Finally, the systolic and diastolic time intervals are determined (Step 26). The process, which is performed using measurement device 10 in conjugation with a computer, will be described in more detail in the following figures.

Figure 3:
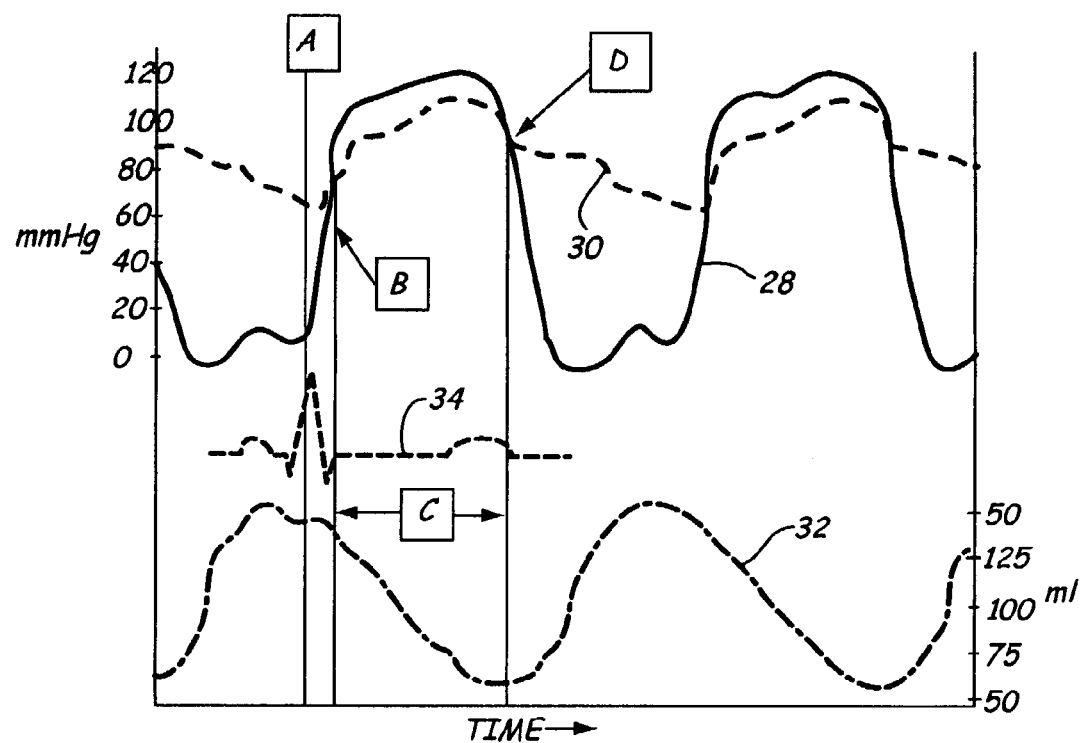
FIG. 3 is a graph comparing left ventricular pressure, arterial pressure, and left ventricular volume over time.

Typically, cardiac cycles are viewed as waveforms. FIG. 3 illustrates the relationship between LV pressure relative to arterial pressure and LV volume. FIG. 3 includes LV pressure waveform 28, arterial pressure waveform 30, and LV volume waveform 32. Electrocardiogram 34 is seen as an insert in the middle of the graph. At "A," diastole is at an end and systole is beginning. Immediately after this point (and prior to point "B"), LV pressure rises, but LV volume remains unchanged, and arterial pressure continues to drop. This is the isovolumic contraction phase of the cardiac cycle. At "B," LV pressure reaches arterial pressure, after which the aortic valve opens as LV pressure exceeds arterial pressure. During time period "C" (the time between points "B" and "D"), IV pressure remains higher than arterial pressure creating a pressure gradient that drives blood out of the ventricle and into the systemic vascular system. Also during this period, LV volume decreases as blood is ejected from the left ventricle.

As systole ends and diastole begins, LV pressure declines. When LV pressure falls below arterial pressure, the aortic valve closes ("D"). Immediately after this point, LV pressure continues to decline while LV volume remains relatively constant (isovolumic relaxation). During this time, arterial pressure declines more slowly than LV pressure and continues to decline until the next systolic event causes arterial pressure to rise again. Once LV pressure falls below left atrial/pulmonary venous pressure, LV filling occurs with little change in LV pressure.

Figure 4:
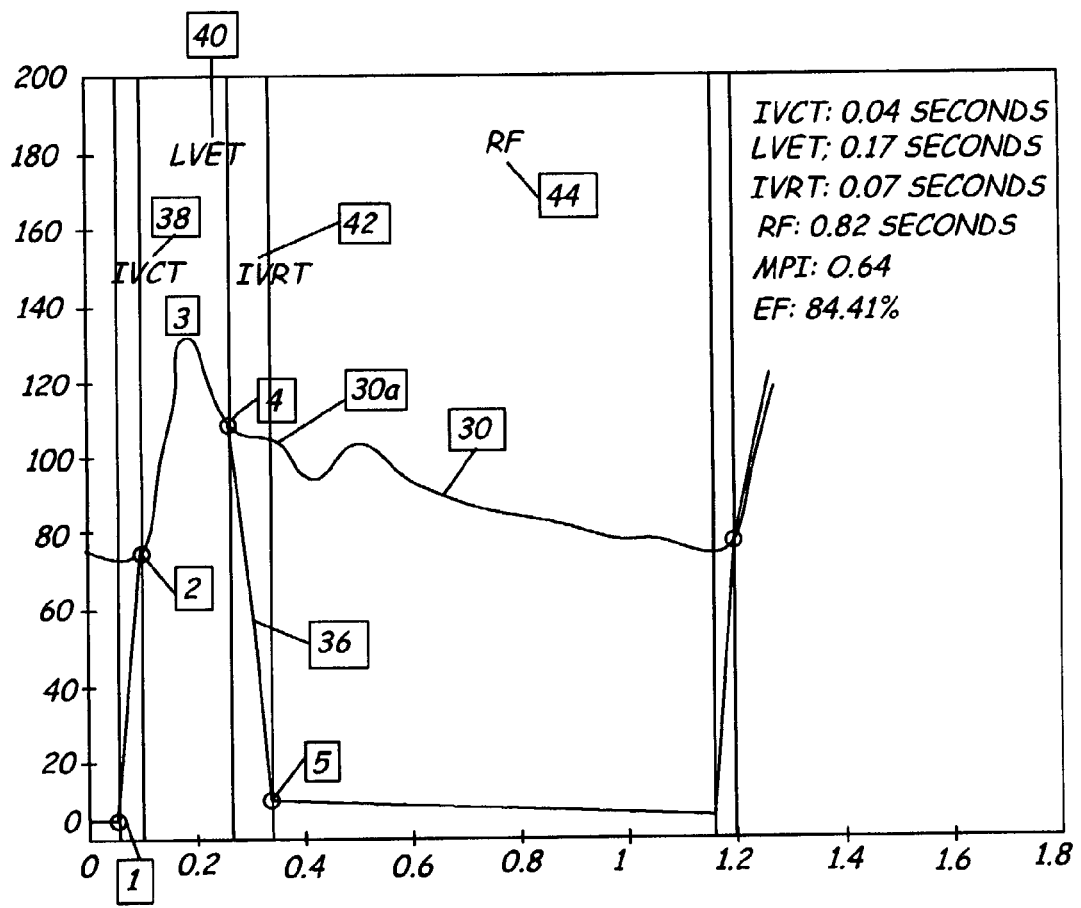
FIG. 4 is a graph relating cardiac events to a derived left ventricular pressure waveform.

With the present invention, the arterial pressure waveform is used to estimate essential points on the LV pressure waveform, so that systolic and diastolic time intervals can be determined. FIG. 4 graphically illustrates how arterial pressure waveform 30 with dichrotic notch 30a is used to calculate LV pressure waveform 36. LV pressure waveform 36 is then used to determine isovolumic contraction time (IVCT) 38, left ventricular ejection time (LVET) 40, isovolumic relaxation time (IVRT) 42, and rapid filling (RF) 44.

Portions of an LV pressure waveform can be estimated from the shape of an arterial pressure waveform. More specifically, as shown in FIG. 4, the portion of arterial pressure waveform 30 labeled 2-3-4 can be used to estimate the portion labeled 1-2-3-4-5 of LV pressure waveform 36. This is based on the observation that the portions 1-2 and 4-5 of LV pressure waveform 36 are of a first order linear, second order linear, or exponential nature. In other words, these portions of LV pressure waveform 36 are quite regular extrapolations of the neighboring portions of arterial pressure waveform 30. This aspect of the present invention is based on the fact that LV pressure waveform 36 does not vary unpredictably, and therefore, it can be derived from arterial pressure waveform 30 because of its predictable nature.

The method extrapolates the 2-3 portion of arterial pressure waveform 30 with a second order curve and determines point 1 as being the inter-section of such a second order curve with a constant pressure of approximately 5 mmHg. In a similar way, the portion 2-4 of arterial pressure waveform 30 is extrapolated using a second order curve and point 5 is determined by intersecting this extrapolated curve with another constant pressure of, for example, 10 mmHg. Point 4 is determined as preceding the dichrotic notch 30a of arterial pressure waveform 30. Once points 1, 2, 3, 4 and 5 are determined, IVCT 38, LVET 40, IVRT 42 and RF 44 times are easily determined.

Notice, however, that the pressure waveforms do not have to be based on blood pressure. The values measured to determine LV pressure waveform 36 are a function of pressure, but it is not necessary to measure actual blood pressure.

The feasibility of using Vasotrac-obtained waveform in identifying pharmacologically induced changes on the cardiovascular system by measuring IVCT, LVET, and IVRT was tested. Each one of ten study subjects had a radial artery catheter inserted and connected to an arterial blood pressure monitoring (Spacelabs) system. On the opposite arm, a Vasotrac sensor simultaneously and continually provided pressure pulse waveform information.

Randomized short-term IV infusion of isoproterenol, nitropruside, and phenylephrine were administered with sufficient time to achieve a steady state. A total of 2,884 pulse waves were analyzed. IVCT, LVET, and IVRT were derived using a specific algorithm.

As shown in FIG. 5, measurable and significant ($p<0.01$)* changes in the values for IVCT, LVET, and IVRT from baseline are reflected by the waveform obtained from the Vasotrac system. The time is the mean time in seconds, and the standard deviation follows in parentheses.

There were significant changes in systolic and diastolic time intervals with the beta-stimulant isoproterenol, and the vasoactive drug phenylephrine (alfa-specific), while nitropruside, produced a significant blood pressure change but only minor changes in IVCT, LVET and IVRT. The changes reflected by the Vasotrac system were quantitatively similar to that obtained via invasive catheterization. The Vasotrac waveform can provide valuable and accurate information for monitoring the cardiovascular response to pharmacological agents exerting a primary effect on the cardiovascular system. These results show that the present invention is useful for early detection of cardiovascular disease states of patients. Additionally, the present invention provides a method of monitoring changes in patients cardiac time intervals noninvasively, which reduces both the cost and risk factors.

The Vasotrac waveforms were similar in morphology with those obtained by invasive A-line placement. The changes in systolic and diastolic time intervals appear to reflect the pharmacological sites of action from the tested cardiovascular drugs.

Although the present invention has been described with reference to preferred embodiments, workers skilled in the art will recognize that changes may be made in form and detail without departing from the spirit and scope of the invention.

What is claimed is:

1. A method of determining cardiac time intervals of a patient, the method comprising:
    measuring arterial pulse values;
    extrapolating left ventricular waveform data from the arterial pulse values;
    identifying main cardiac events based on the left ventricular waveform data; and deriving systolic and diastolic time intervals based on the main cardiac events.

2. The method of claim 1 wherein the arterial pulse values are measured noninvasively.

3. The method of claim 1 wherein the arterial pulse valves are measured invasively.

4. The method of claim 1 wherein the arterial pulse is a radial pulse.

5. The method of claim 1 wherein the main cardiac events include isovolumic contraction time, left ventricular ejection time; isovolumic relaxation time, and rapid filling time.

6. The method of claim 1 wherein identifying the main cardiac events further comprises:
    generating an arterial pulse waveform from the arterial pulse values;
    extrapolating the left ventricular waveform data from a portion of the arterial pulse waveform; and
    identifying a point where the left ventricular waveform data intersects with a preselected constant pressure, wherein the identified point corresponds to one of the main cardiac events.

7. The method of claim 6 wherein the portion of the arterial pulse waveform produces waveforms for the left ventricular waveform data that are selected from the group consisting of first order linear, second order linear, and exponential waveforms.

8. The method of claim 1 and further comprising:
    measuring changes in the cardiac time intervals for early detection of cardiovascular disease.

9. The method of claim 1 and further comprising:
    infusing the patient with pharmacological agents; and
    measuring changes in the systolic and diastolic time intervals of the patient.

10. The method of claim 1 wherein the arterial pulse values are arterial blood pressure values.

11. The method of claim 1 and further comprising:
    generating arterial pulse waveform data based on the arterial pulse values; and
    using the arterial pulse waveform data to generate the left ventricular waveform data.

12. The method of determining cardiac information of a patient, the method comprising:
    measuring arterial pulse values; and
    extrapolating left ventricular waveform data from the arterial pulse values.

13. The method of claim 12 wherein the arterial pulse values are based on arterial pulse blood pressure values.

14. An apparatus for determining cardiac time intervals, the apparatus comprising:
    an arterial pressure measurement device;
    means for generating arterial pulse waveform data;
    means for extrapolating left ventricular waveform data;
    means for identifying main cardiac events; and
    means for deriving systolic and diastolic time intervals.

15. The apparatus in claim 14 wherein the arterial pressure measurement device is a noninvasive blood pressure measurement device.

16. The apparatus of claim 14 wherein the arterial pressure measurement device is an invasive arterial line.

17. The apparatus of claim 14 wherein the means for identifying main cardiac events further comprises:
    software for identifying the main cardiac events from the arterial pulse waveform data and from the left ventricular waveform data.

* * * * *